United States Patent [19]

Baum

[11] 4,254,050

[45] Mar. 3, 1981

[54] PREPARATION OF ESTERS

[75] Inventor: Jonathan S. Baum, Pennington, N.J.

[73] Assignee: FMC Corporation, Philadelphia, Pa.

[21] Appl. No.: 156,958

[22] Filed: Jun. 6, 1980

Related U.S. Application Data

[63] Continuation-in-part of Ser. No. 79,622, Sep. 27, 1979, abandoned.

[51] Int. Cl.$^3$ .................. C07C 120/00; C07C 121/75
[52] U.S. Cl. ................................................. 260/465 D
[58] Field of Search .................................... 260/465 D

[56] References Cited

U.S. PATENT DOCUMENTS

| | | | |
|---|---|---|---|
| 3,835,176 | 9/1974 | Matsuo et al. | 260/465 D |
| 4,024,163 | 5/1977 | Elliott et al. | 260/465 D X |
| 4,110,363 | 8/1978 | Sheldon | 260/465 D |

FOREIGN PATENT DOCUMENTS

| | | |
|---|---|---|
| 52-142046 | 11/1977 | Japan . |
| 1439615 | 6/1976 | United Kingdom . |
| 2000764 | 1/1979 | United Kingdom . |

OTHER PUBLICATIONS

Normant et al., *Synthesis*, 805, (1975).
Vander Zwan et al., J. Org. Chem., vol. 43, 2655, (1978).

*Primary Examiner*—Dolph H. Torrence
*Attorney, Agent, or Firm*—Richard L. Hansen; Henry R. Ertelt

[57] ABSTRACT

Certain alpha-cyano esters are prepared by reacting an acyl halide with an aldehyde in a substantially water-immiscible aprotic solvent and an aqueous solution of water-soluble cyanide salt in the presence of an amine or cryptate rate-promoting agent.

9 Claims, No Drawings

PREPARATION OF ESTERS

This is a continuation-in-part of application Ser. No. 079,622, filed Sept. 27, 1979, abandoned.

This invention relates to a process for preparing esters of carboxylic acids, more specifically, esters which contain a cyano group bonded to the alpha-carbon atom in the alcohol portion of the ester molecule.

Esters with a cyano group so situated are prepared by reacting an acid with the appropriate cyanohydrin. According to U.S. Pat. No. 3,835,176, the reaction can also be effected by treating an acyl halide with a mixture of the appropriate aldehyde and aqueous sodium or potassium cyanide, optionally in an aprotic solvent. It is disclosed, for example, that 3-phenoxy-α-cyanobenzyl chrysanthemate is prepared in 64% yield by reacting chrysanthemoyl chloride, 3-phenoxybenzaldehyde, and an aqueous solution of sodium cyanide at 0° C. for 1 hour.

U.S. Pat. No. 4,110,363 discloses a variation of this process which employs, in addition to the acyl halide, the aldehyde, and the water-soluble cyanide, a mixture of water, a water-immiscible aprotic solvent, and a macrocyclic polyether or "crown ether" catalyst. Using the preferred 18-crown-6 as the catalyst, for example, the commercial insecticidal ester, α-cyano-3-phenoxybenzyl 3-(2,2-dichloroethenyl)-2,2-dimethylcyclopropanecarboxylate, is prepared in 76% yield at room temperature in a reaction time of 2 hours. Were is possible to shorten the reaction time and increase the yield, producing this and other alpha-cyano esters by reacting an acyl halide with an aldehyde and a cyanide would be of great commercial interest. Insecticidal alpha-cyano esters whose preparations would be facilitated include α-cyano-3-phenoxybenzyl 3-(2,2-dichloroethenyl)-2,2-dimethylcyclopropanecarboxylate and α-cyano-3-phenoxybenzyl 3-(2,2-dibromoethenyl)-2,2-dimethylcyclopropanecarboxylate, whose insecticidal activity is disclosed in U.S. Pat. No. 4,024,163, incorporated by reference herein. Other insecticidal alpha-cyano esters of particular interest are α-cyano-3-phenoxybenzyl 3-(2-chloro-3,3,3-trifluoropropenyl)-2,2-dimethylcyclopropanecarboxylate, α-cyano-3-phenoxybenzyl 2,2,3,3-tetramethylcyclopropanecarboxylate, and α-cyano-3-phenoxybenzyl 2-(4-chlorophenyl)-3-methylbutanoate, whose activity is disclosed in Great Britain Pat. No. 2,000,764, U.S. Pat. No. 3,835,176, and Great Britain Pat. No. 1,439,615, respectively, all of which are incorporated herein by reference.

One advantage of this invention is that it provides a process for making alpha-cyano esters in very high yield in a short time. Another advantage of this invention is that it provides an esterification process whose product does not require lengthy and expensive purification.

Accordingly, this invention provides a method to prepare an insecticidal alpha-cyano ester by reacting an acyl halide with an aldehyde in a mixture of substantially water-immiscible aprotic solvent and an aqueous solution of water-soluble cyanide salt in the presence of a catalytic amount of rate-promoting agent selected from tertiary amines, polyamines, and cryptates. Either the acyl halide or the aldehyde may exhibit optical or geometric isomerism, which is not affected by the reaction.

In a preferred embodiment, there is provided a process for preparing an insecticidal α-cyano-3-phenoxybenzyl ester of the formula

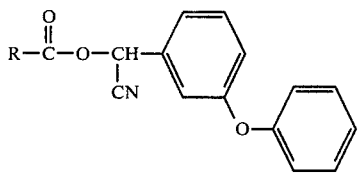

wherein R is selected from 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, 2,2,3,3-tetramethylcyclopropyl, and 1-(4-chlorophenyl)-2-methylpropyl which comprises reacting an acyl halide of the formula

wherein X is chlorine or bromine and R is as defined above with 3-phenoxybenzaldehyde in a mixture of substantially water-immiscible aprotic solvent and an aqueous solution of water-soluble cyanide salt in the presence of a catalytic amount of rate-promoting agent selected from tertiary polyamines and cryptates.

The process of this invention is especially effective in producing a high yield of insecticidal α-cyano-3-phenoxybenzyl esters in a short time when R is 3-(2,2-dichloroethenyl)-2,2-dimethylcyclopropyl, 3-(2,2-dibromoethenyl)-2,2-dimethylcyclopropyl, or 3-(2-chloro-3,3,3-trifluoropropenyl)-2,2-dimethylcyclopropyl, and outstanding results are obtained when R is 3-(2,2-dichloroethenyl)-2,2-dimethylcyclopropyl.

Although the process of this invention is especially advantageous when R is selected from the groups named above, the process is also effective in producing other alpha-cyano esters wherein R is an aliphatic or aromatic group, which may optionally contain various substituents. Although the process of this invention is preferably employed to produce α-cyano-3-phenoxybenzyl esters by using 3-phenoxybenzaldehyde as a reactant, the process is equally suited to the production of other alpha-cyano esters by varying the type of aldehyde employed in the process.

Various aprotic solvents which are substantially water-immiscible may be used in the process. Any alkyl, haloalkyl, aryl, haloaryl, aralkyl, haloaralkyl, or cyclic hydrocarbon, provided that it is a liquid at temperatures between about 0° C. and 50° C. and forms a discrete second phase when mixed with water, may be used. Such solvents include iso-hexane, 3-methylpentane, 2,3-dimethylbutane, 2,2-dimethylbutane, n-heptane, n-octane, petroleum ether, ligroin, n-propyl bromide, n-propyl iodide, n-butyl chloride, n-butyl bromide, n-pentyl chloride, n-pentyl bromide, diethyl ether, dipropyl ether, dibutyl ether, benzene, toluene, and xylene, for example. Among these solvents, n-heptane is preferred because it is readily available and inexpensive.

A number of water-soluble cyanide salts may be used; for example, the salt may be an alkali metal cyanide such as lithium, sodium, potassium, rubidium, or cesium cyanide, or mixtures thereof. Among these, sodium cyanide generally is preferred. However, when it is desired to use certain cryptates as rate-promoting agents, it may be desirable to substitute lithium or potassium cyanide as described below.

The cyanide salt is dissolved in water, the amount of water employed being relatively small, but preferably sufficient to keep all of the cyanide salt in solution under the reaction conditions. In the case that the salt is sodium cyanide, the preferred molar ratio of water to sodium cyanide is between about 3.5 and 6, preferably about 4.5.

The process of this invention is conducted in the pressence of a catalytic amount of rate-promoting agent selected from tertiary amines, polyamines, and cryptates. For purposes of this invention, a catalytic amount of rate-promoting agent is in the range 1–5 mole percent based on aldehyde, advantageously about 2 mole percent.

The rate-promoting agent may be a tertiary amine or polyamine, a tertiary polyamine being a compound containing more than one tertiary amino nitrogen atom. Particularly desirable tertiary polyamines are linear tertiary polyamines of the formula

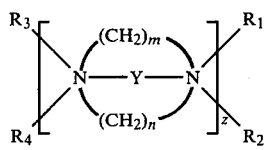

wherein Y is —(CH$_2$)$_k$— with k being 1–6, C$_3$–C$_7$ cycloalkane, C$_2$–C$_6$ alkenyl, or C$_2$–C$_6$ alkynyl; z is 1 or 2, and when z is 1, m and n are 0 or independently 1–6, and when m and n are 0, R$_1$, R$_2$, R$_3$, and R$_4$ are hydrocarbon groups, and R$_1$ may be joined with R$_2$, and R$_3$ may be joined with R$_4$ to form a ring containing the N atom to which both are joined, and when m is 1–6 and n is 0, R$_1$ and R$_3$ are absent, and R$_2$ and R$_4$ are hydrocarbon groups, and when both m and n are at least 1, R$_2$ and R$_4$ are absent; and when z is 2, m and n are 0, R$_1$ and R$_3$ are hydrocarbon groups and R$_2$ and R$_4$ are absent.

Particularly useful linear tertiary polyamines within the aforesaid description are 2,4-dimethyl-2,4-diazapentane, 2,5-dimethyl-2,5-diazahexane, 1,1'-(1,2-ethanediyl)bis-[piperidine], N,N,N',N'-tetramethyl-1,2-diaminocyclohexane, 1,4-dimethyl-1,4-diazacyclohexane, diazabicyclo[2.2.2]octane, 2,6-dimethyl-2,6-diazaheptane, 2,7-dimethyl-2,7-diazaoctane, 2,7-dimethyl-2,7-diaza-4-octene, 2,7-dimethyl-2,7-diaza-4-octyne, 2,9-dimethyl-2,9-diazadecane, and 2,5,8,11-tetramethyl-2,5,8,11-tetraazadodecane. Among these compounds, diazabicyclo[2.2.2]octane, 2,6-dimethyl-2,6-diazaheptane, 2,7-dimethyl-2,7-diazaoctane, and 2,5,8,11-tetramethyl-2,5,8,11-tetrazadecane are preferred, and diazabicyclo[2.2.2]octane is especially attractive.

Macrocyclic tertiary polyamines such as 1,4,8,11-tetraazacyclotetradecane, for example, are also useful, as are sparteine and hexamethylenetetraamine.

Cryptates, polyoxadiazamacrobicycles, constitute another class of rate-promoting agent useful in the practice of this invention. Cryptates of the formula

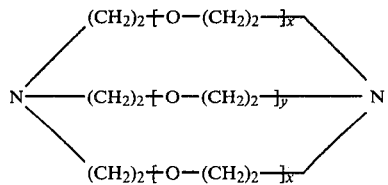

wherein x and y are independently 1 or 2 are especially useful. When the cyanide salt is sodium cyanide 4,7,13,16,21-pentaoxa-1,10-diazabicyclo[8.8.5]tricosane is preferred, but when lithium cyanide is employed 4,7,13,18-tetraoxa-1,10-diazabicyclo[8.5.5]eicosane should be used, and 4,7,13,16,21,24-hexaoxy-1,10-diazabicyclo[8.8.8]hexacosane is preferred when potassium cyanide is employed.

The process of this invention is carried out between approximately equimolar amounts of the acyl halide, preferably the acyl chloride, aldehyde and aqueous solution of cyanide salt in the water-immiscible aprotic solvent, but slight excesses of the acyl halide and cyanide salt are typically used. The acyl halide may be added last, preferably dropwise, to the stirred reaction mixture, but it is preferred to add a solution containing aldehyde and acyl halide to a stirred mixture of aqueous cyanide salt and water-immiscible aprotic solvent. Although the reaction can be carried out over a wide temperature range, the range 0°–50° C. is satisfactory in most cases, and it is preferred to carry out the reaction at room temperature, since neither external heating nor cooling are then required.

The process will be understood more readily by reference to the following Examples, which illustrate it. Temperatures are in degrees Celsius. The reactions exemplified were, in many cases, monitored by gas liquid partition chromatography (glpc), and the time required for disappearance of the limiting reagent after beginning addition of the acyl halide was determined, together with the amount of alpha-cyano ester produced at that time.

EXAMPLE 1

Preparation of α-cyano-3-phenoxybenzyl 3-(2,2-dichloroethenyl)-2,2-dimethylcyclopropanecarboxylate A. Using diazabicyclo[2.2.2]octane (1) A flask was charged with 3-phenoxybenzaldehyde (1.98 g, 10.0 mmole), sodium cyanide (0.59 g, 12 mmole), 20 ml n-heptane, 1 ml water, and diazabicyclo[2.2.2]octane (0.022 g, 0.2 mmole). This mixture was vigorously stirred, and 3-(2,2-dichloroethenyl)-2,2-dimethylcyclopropanecarbonyl chloride (2.38 g, 10.5 mmole) was added in one portion. Stirring was continued at room temperature for one hour, at which time glpc indicated a 94% yield of the desired alpha-cyano ester. The mixture was filtered. The filter cake was washed twice with 10 ml portions of diethyl ether. The filtrate was dried over magnesium sulfate, and the heptane was stripped under reduced pressure to yield the desired ester as a residual oil (4.10 g).

Use of the optically active (1R,cis) carbonyl chloride in the aforesaid process afforded the corresponding optically active ester in 96% yield within 1 hr. reaction time.

(2) Under a dry nitrogen atmosphere a mixture of sodium cyanide (5.9 g, 0.12 mole) and 1,4-diazabicyclo[2.2.2]octane (0.22 g, 0.002 mole) in 10 grams of water was stirred at room temperature. During a one hour period a solution of 3-phenoxybenzaldehyde (20.6 g, 0.1 mole) and 3-(2,2-dichloroethenyl)-2,2-dimethylcyclopropanecarbonyl chloride (24.1 g, 0.105 mole) in 120 ml of n-octane was added to the reaction mixture. After complete addition, the reaction mixture was stirred for one hour. An aqueous solution containing 20% sodium carbonate was added to the reaction mixture and the total warmed to 60°. The organic phase was separated and washed with water, dried over anhydrous magnesium sulfate and filtered. The solvent was removed from the filtrate under reduced pressure to yield α-cyano-3-phenoxybenzyl 3-(2,2-dichloroethenyl)-2,2-dimethylcyclopropanecarboxylate.

B. Using 2,6-dimethyl-2,6-diazaheptane

A flask was charged with a solution of 3-phenoxybenzaldehyde (1.98 g, 10 mmole) in 10 ml n-heptane. This solution was cooled to 10°, then 2,6-dimethyl-2,6-diazaheptane (26 mg, 0.2 mmole), sodium cyanide (0.59 g, 12 mmole), and 1 ml water were added. 3-(2,2-Dichloroethenyl)-2,2-dimethylcyclopropanecarbonyl chloride (2.38 g, 10.5 mmole) was then added in one portion with stirring, and the temperature of the reaction mixture was maintained at 8°–12°. After 45 minutes, glpc indicated a 93% yield of the desired alpha-cyano ester. After a total of 1.25 hours, the reaction mixture was filtered. The filter cake was washed with ether, and the solvent was evaporated from the filtrate, affording the desired ester (4.3 g).

C. Using 2,5,8,11-tetramethyl-2,5,8,11-tetraazadodecane

A flask equipped with a stirrer, addition funnel, and an inlet for nitrogen gas was charged with sodium cyanide (0.59 g, 0.012 mole) dissolved in 1 ml water, 2,5,8,11-tetramethyl-2,5,8,11-tetraazadodecane (0.048 g, 0.2 mmole) in 3 ml heptane, and 3-phenoxybenzaldehyde (1.98 g, 0.01 mole) in 7 ml heptane. The reactants were mixed under a nitrogen atmosphere. 3-(2,2-Dichloroethenyl)-2,2-dimethylcyclopropanecarbonyl chloride (2.38 g, 0.0105 mole) in 10 ml heptane was added dropwise to the stirred mixture over a period of 20 minutes. Twenty minutes later, a total of 40 minutes, glpc indicated a 93% yield of the desired ester. The reaction mixture was stirred for another 40 minutes, then poured into a separatory funnel, diluted with 40 ml diethyl ether, washed once with a 1 N aqueous solution of sodium hydroxide, three times with water, and once with saturated aqueous sodium chloride solution. After phase separation, the separated ethereal layer was dried over magnesium sulfate, and the solvent was evaporated, affording the ester as a pale yellow oil (4.02 g).

D. Using 4,7,13,16,21-pentaoxa-1,10-diazabicyclo[8.8.5]tricosane

A flask was charged with 3-phenoxybenzaldehyde (1.98 g, 10 mmole), 10 ml n-heptane, 4,7,13,16,21-pentaoxa-1,10-diazabicyclo[8.8.5]tricosane (66 mg, 0.2 mmole), sodium cyanide (0.59 g, 12 mmole), 1 ml water, and a solution of 3-(2,2-dichloroethenyl)-2,2-dimethylcyclopropanecarbonyl chloride (2.38 g, 10.5 mmole) in 10 ml n-heptane. The reaction mixture was stirred, and an exotherm (to approximately 40°) was observed after 20 minutes. After 50 minutes, glpc showed a 99% yield of the desired ester. The reaction mixture was filtered, diluted with ether, dried over magnesium sulfate, and the solvent was evaporated to afford the desired ester (3.90 g).

E. Using Tetramethylethylene Diamine

A solution of 3-(2,2-dichloroethenyl)-2,2-dimethylcyclopropanecarbonyl chloride (114 g, 0.315 mole) and 3-phenoxybenzaldehyde (61.9 g, 0.3 mole) in 275 ml of n-heptane was added dropwise under nitrogen in one hour to a stirred mixture of sodium cyanide (18 g, 0.36 mole), tetramethylethylene diamine (0.7 g, 0.006 mole), and 30 g of water at about 40°. After the addition, the reaction mixture was stirred for 90 minutes at about 40°. The reaction mixture was worked up as in Example 1A.(2), producing the desired ester.

F. Using Tetramethyl-1,6-hexane Diamine

By the method of Example 1E. above, but substituting tetramethyl-1,6-hexane diamine for tetramethylethylene diamine, α-cyano-3-phenoxybenzyl 3-(2,2-dichloroethenyl)-2,2-dimethylcyclopropanecarboxylate was prepared.

The preparation of α-cyano-3-phenoxybenzyl 3-(2,2-dichloroethenyl)-2,2-dimethylcyclopropanecarboxylate using other rate-promoting agents under otherwise similar conditions gave the results shown in Table 1.

EXAMPLE 2

Preparation of α-cyano-3-phenoxybenzyl 3-(2,2-dibromoethenyl)-2,2-dimethylcyclopropanecarboxylate using diazabicyclo[2.2.2]octane A flask was charged with 3-phenoxybenzaldehyde (1.98 g; 10.0 mmole), 10 ml n-heptane, diazabicyclo[2.2.2]octane (22 ml, 0.2 mmole), sodium cyanide (0.59 g, 12 mmole), and 1 ml water. 3-(2,2-Dibromoethenyl)-2,2-dimethylcyclopropanecarbonyl chloride (3.32 g, 10.5 mmole) in 10 ml n-heptane was added with stirring. After 2 hours, the reaction mixture was filtered, the filter cake was washed with 30 ml of ether, and the filtrate was dried over magnesium sulfate. The solvent was stripped, affording the desired ester as a yellow oil (4.4 g, 96% yield).

EXAMPLE 3

Preparation of α-cyano-3-phenoxybenzyl 3-(2-chloro-3,3,3-trifluoropropenyl)-2,2-dimethylcyclopropanecarboxylate using 2,7-dimethyl-2,7-diazaoctane A flask was charged with 3-phenoxybenzaldehyde (1.98 g, 10 mmole), 10 ml n-heptane, 2,7-dimethyl-2,7-diazaoctane (29 mg, 0.2 mmole), sodium cyanide (0.59 g, 12 mmole) and 1 ml water. 3-(2-Chloro-3,3,3-trifluoropropenyl)-2,2-dimethylcyclopropanecarbonyl chloride (2.0 g, 10.5 mmole) dissolved in 10 ml n-heptane was then added in one portion. After 1.3 hr., the conversion was complete. The reaction mixture was stirred for 4.5 hr, when 5 ml diethyl ether and 5 ml 1 N aqueous sodium hydroxide solution were added. The resultant mixture was stirred for 1.5 hr and the two phases separated. The organic phase was washed once with 1 N aqueous sodium hydroxide solution, once with water, and once with a saturated aqueous sodium chloride solution, then dried over magnesium sulfate, filtered, and the solvent distilled off under reduced pressure to afford the desired ester (4.1 g, 91% yield).

EXAMPLE 4

Preparation of α-cyano-3-phenoxybenzyl 2,2,3,3-tetramethylcyclopropanecarboxylate using 2,6-dimethyl-2,6-diazaheptane A flask was charged with 3-phenoxybenzaldehyde (3.16 g, 16 mmole), 10 ml n-heptane, 2,6-dimethyl-2,6-diazaheptane (26 mg, 0.2 mmole), sodium cyanide (0.94 g, 19.2 mmole) and 1 ml water. 2,2,3,3-Tetramethylcyclopropanecarbonyl chloride (2.6 g, 16.7 mmole) dissolved in 10 ml n-heptane was added next, in one portion. An exotherm (to approximately 38°) was observed upon addition of the acid chloride. Analysis indicated a 74% yield of the desired ester in 4 hours. After cooling, the reaction mixture was filtered, diluted with diethyl ether, dried over magnesium sulfate, and distilled under reduced pressure to afford an orange residual oil. The oil was dissolved in 25 ml diethyl ether, and the resultant ethereal solution was mixed for 2 hr. with a 1 N aqueous sodium hydroxide solution. After phase separation, the ethereal layer was washed once with water, once with a saturated aqueous sodium chloride solution, dried over magnesium sulfate, and the solvent was distilled under reduced pressure to afford the desired ester (3.0 g).

EXAMPLE 5

Preparation of α-cyano-3-phenoxybenzyl 2-(4-chlorophenyl)-3-methyl butanoate A. Using diazabicyclo[2.2.2]octane A flask was charged with 3-phenoxybenzaldehyde (1.98 g, 10 mmole), 10 ml n-heptane, diazabicyclo[2.2.2]octane (22 mg, 0.2 mmole), sodium cyanide (0.59 g, 12 mmole), and 1 ml water, and stirring was begun. 2-(4-Chlorophenyl)-3-methylbutanoyl chloride (2.42 g, 10.5 mmole) in 10 ml n-heptane was then added in one portion. The reaction mixture was stirred at room temperature for 1 hr at which time glpc indicated a 74% yield of the desired ester. Stirring was continued overnight, then the reaction mixture was filtered, diluted with diethyl ether, and the solvent was distilled under reduced pressure to afford the desired ester as the residue (4.02 g).

B. Using 2,5,8,11-tetramethyl-2,5,8,11-tetraazadodecane

A flask was charged with 3-phenoxybenzaldehyde (1.98 g, 10 mmole), 20 ml n-heptane, 2,5,8,11-tetramethyl-2,5,8,11-tetraazadodecane (0.046 g), sodium cyanide (0.59 g, 12 mmole), and 1 ml. water. With stirring, 2-(4-chlorophenyl)-3-methylbutanoyl chloride (2.42 g, 10.5 mmole) was added dropwise over a period of 6 minutes. The reaction mixture was stirred at room temperature. Analysis by glpc 2.4 hr. after the acyl chloride had been added indicated a 67.7% yield of the desired ester. Stirring was continued overnight, and the desired ester (3.4 g) was isolated as described in the preceding Example.

TABLE 1

PREPARATION OF α-CYANO-3-PHENOXYBENZYL-3-(2,2-DICHLORO-ETHENYL)-2,2-DIMETHYLCYCLOPROPANECARBOXYLATE USING OTHER RATE-PROMOTING AGENTS

| Rate-Promoting Agent | Reaction Time | Yield |
|---|---|---|
| tri-n-hexylamine | 4.5 hours | 82% |
| triethylamine | 2 hours | 89% |
| 2,4-dimethyl-2,4-diazapentane | 24 hours | 96% |
| 2,5-dimethyl-2,5-diazahexane | 0.5 hour | 91% |
| 2,9-dimethyl-2,9-diazadecane | 1.0 hour | 96% |
| 1,1'-(1,2-ethanediyl)-bis[piperidine] | 1.0 hour | 94% |
| 1,4-dimethyl-1,4-diazacyclohexane | 1.0 hour | 86% |
| N,N,N',N'-tetramethyl-1,2-diaminocyclohexane | 1.5 hours | 96% |
| 1,4,8,11-tetramethyl-1,4,8,11-tetraazacyclotetradecane | 1.5 hours | 96% |
| (—)-sparteine | 1.3 hours | 95% |

I claim:

1. A process for preparing an insecticidal α-cyano-3-phenoxybenzyl ester of the formula

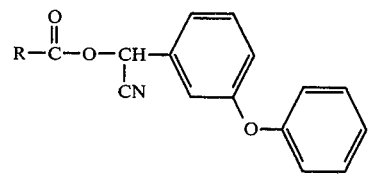

wherein R is selected from 3-(2,2-dichloroethenyl)-2,2-dimethylcyclopropyl, 3-(2,2-dibromoethenyl)-2,2-dimethylcyclopropyl, 3-(2-chloro-3,3,3-trifluoropropenyl)-2,2-dimethylcyclopropyl, 2,2,3,3-tetramethylcyclopropyl, and 1-(4-chlorophenyl)-2-methylpropyl which comprises reacting an acyl halide of the formula

wherein X is chlorine or bromine and R is as defined above with 3-phenoxybenzaldehyde in a mixture of substantially water-immiscible aprotic solvent and an aqueous solution of water-soluble cyanide salt in the presence of a catalytic amount of rate-promoting agent selected from tertiary polyamines which are linear tertiary polyamines of the formula

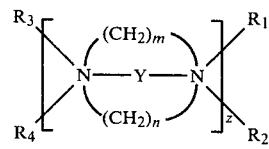

wherein Y is —$(CH_2)_k$— with k being 1-6, $C_3$–$C_7$ cycloalkane, $C_2$–$C_6$ alkenyl, or $C_2$–$C_6$ alkynyl; z is 1 or 2, and when z is 1, m and n are 0 or independently 1-6, and when m and n are 0, $R_1$, $R_2$, $R_3$, and $R_4$ are hydrocarbon groups, and $R_1$ may be joined with $R_2$, and $R_3$ may be joined with $R_4$ to form a ring containing the N atom to which both are joined, and when m is 1-6 and n is 0, $R_1$ and $R_3$ are absent, and $R_2$ and $R_4$ are hydrocarbon groups, and when both m and n are at least 1, $R_2$ and $R_4$ are absent; and when z is 2, m and n are 0, $R_1$ and $R_3$ are hydrocarbon groups and $R_2$ and $R_4$ are absent, 1,4,8,11-tetramethyl-1,4,8,11-tetraazacyclotetradecane, sparteine, and cryptates.

2. The process of claim 1 wherein the linear tertiary polyamine is selected from 2,4-dimethyl-2,4-diazapentane, 2,5-dimethyl-2,5-diazahexane, 1,1'-(1,2-ethanediyl)-bis[piperidine], N,N,N',N'-tetramethyl-1,2-diaminocyclohexane, 1,4-dimethyl-1,4-diazacyclohexane, diazabicyclo[2.2.2]octane, 2,6-dimethyl-2,6-diazaheptane, 2,7-dimethyl-2,7-diazaoctane, 2,9-dimethyl-2,9-diazadecane, and 2,5,8,11-tetramethyl-2,5,8,11-tetraazadodecane.

3. The process of claim 2 wherein the linear tertiary polyamine is diazabicyclo[2.2.2]octane, 2,6-dimethyl-2,6-diazaheptane, 2,7-dimethyl-2,7-diazaoctane, or 2,5,8,11-tetramethyl-2,5,8,11-tetraazadecane.

4. The process of claim 1 wherein the ratepromoting agent is diazabicyclo[2.2.2]octane.

5. The process of claim 1 wherein the ratepromoting agent is a cryptate of the formula

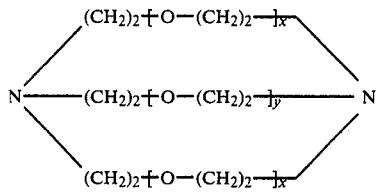

wherein x and y are independently 1 or 2.

6. The process of claim 5 wherein the cryptate is 4,7,13,16,21-pentaoxo-1,10-diazabicyclo[8.8.5]tricosane.

7. The process according to any one of claims 1, 2, 3, 4, 5, or 6 wherein R is 3-(2,2-dichloroethenyl)-2,2-dimethylcyclopropyl.

8. A process according to any one of claims 1, 2, 3, 4, 5, or 6 wherein the water-immiscible aprotic solvent is n-heptane.

9. A process according to any one of claims 1, 2, 3, 4, 5, or 6 wherein the water-soluble cyanide salt is sodium cyanide.

* * * * *